United States Patent [19]

Hodge

[11] Patent Number: 5,042,161

[45] Date of Patent: Aug. 27, 1991

[54] INTRAVASCULAR SIZING METHOD AND APPARATUS

[76] Inventor: Joseph Hodge, 1065 Partridge Rd., Spartanburg, S.C. 29302

[21] Appl. No.: 784,727

[22] Filed: Oct. 7, 1985

[51] Int. Cl.$^5$ .............................. G01B 3/34; G01B 3/50
[52] U.S. Cl. .................................. 33/501.45; 33/512; 128/774
[58] Field of Search ............. 33/178 B, 168 B, 143 C, 33/511, 512, 501.45; 128/774

[56] References Cited

U.S. PATENT DOCUMENTS

| | | | |
|---|---|---|---|
| 1,264,519 | 4/1918 | Hinson | 33/178 B |
| 1,514,250 | 11/1924 | Briney | 33/178 B |
| 2,377,020 | 5/1945 | Lundeberg | 33/178 B |
| 2,684,536 | 7/1954 | Ahmer | 33/178 B |
| 2,833,048 | 5/1958 | Telgmann | 33/178 B |
| 4,211,241 | 7/1980 | Kaster et al. | 33/178 B |

Primary Examiner—William A. Cuchlinski, Jr.
Attorney, Agent, or Firm—Dority & Manning

[57] ABSTRACT

A method and apparatus for sizing an intravascular graft which is to be secured on an existing vascular vessel. A sizing gauge having a handle with at least one sizing element of known diameter secured to an end of same is provided. Sizing elements of known diameter are inserted into the lumen of a vessel being grafted, one at a time, until one of a sizing element fits snugly in the lumen. A premanufactured graft is then selected according to the size of the snug-fitting sizing element.

3 Claims, 3 Drawing Sheets

INTRAVASCULAR SIZING METHOD AND APPARATUS

BACKGROUND OF THE INVENTION

This invention relates to apparatus and a method for accurately measuring the interior or lumen diameter of an artery or other vascular vessel to which a graft is to be surgically attached By determining the lumen diameter of the vascular vessel an approximately sized graft can be readily chosen which matches the measured dimension, leading to better connection between the graft and the vessel.

Certain disease processes, such as arteriosclerosis and syphilis, may cause damage to the wall of the aorta for example, resulting in dilation of the aorta and formation of a large bulge, or aneurysm. An aneurysm may produce pain and may disturb the blood flow in tributary vessels of the aorta. Aneurysms may also rupture, leading to possibly fatal internal bleeding. Treatment of an aneurysm involves surgical removal of the enlarged defective section of the vessel followed by replacement with a synthetic tubular element or graft which is surgically formed to the resected portions of the vessel.

One problem that arises in the replacement of a defective arterial or other vascular section with a tubular graft element involves selection of a proper size of the graft for the effected vessel. Such historically has been accomplished by measuring the inside diameter of the vessel with calipers which are bulky, hard to handle by the surgeon and often impractical due to lack of accessibility of the effected vessel portion Trial and error procedures have also been practiced. After the defective section of the vessel has been resected, and the adjacent vessel sections made ready for grafting, a fabric graft, for example, is matched up with the open vessel ends until a graft having a diameter complementary to the size of the exposed ends of the remaining artery sections is found.

While successful grafting of vascular vessels has obviously occurred following conventional surgical procedures, certain problems, noted above, have persisted. The apparatus of the present invention avoids at least certain of the prior art problems and may be employed by the surgeon to facilitate ease and accuracy of graft size selection.

SUMMARY OF THE INVENTION

The present invention provides a method and an apparatus by which a vascular graft may be quickly and accurately matched to the size of the vessel to which it is to be sutured. A vessel sizing gauge is provided having at least one, and preferably a plurality of cylindrical sizing elements of known diameter. After the defective section of a vessel which is to be replaced by the graft has been resected, the sizing apparatus of the present invention is inserted into each of the exposed vascular end sections until a snug fit is achieved with a known diameter sizing section. The known diameter of the snug fitting portion of the apparatus determines the graft size to be employed. Several cylindrical sizing portions, each having a different known diameter, are preferably provided on each end of apparatus of the present invention, with a stepped configuration. A handle having gripping means forms a part of the present apparatus to facilitate ease of manipulation with one hand. The present sizing apparatus may be straight or angulated according to dictates of location of the vessel to be sized.

Should the vessel in which the sizing apparatus is inserted be larger than the particular sizing portion chosen, larger sizing portions on the apparatus are inserted into the vessel until the snug fit is achieved. Once it has been determined which known diameter sizing portion snugly fits within the vessel, a graft having an opening corresponding to the diameter of such sizing element is selected for connection to the vessel. A graft of proper size can thus be quickly and accurately determined.

Accordingly, an object of the present invention is to provide a method and an apparatus for readily sizing an intravascular graft.

Another object of the present invention is to provide a method for determining the inside diameter and cross-section of a vascular vessel to which a graft is to be surgically attached.

Another object of the present invention is to provide improved apparatus for determining the inside diameter of an intravascular vessel.

Still another object of the present invention is to provide a method and an apparatus for simultaneously dilating and measuring the lumen cross-section diameter of an intravascular vessel to which a graft is to be surgically secured.

BRIEF DESCRIPTION OF THE DRAWINGS

The construction designed to carry out the invention will be hereinafter described, together with other features thereof.

The invention will be more readily understood from a reading of the following specification and by reference to the accompanying drawings forming a part thereof, wherein examples of the invention are shown and wherein.

DESCRIPTION OF A PREFERRED EMBODIMENT

Figure 1:
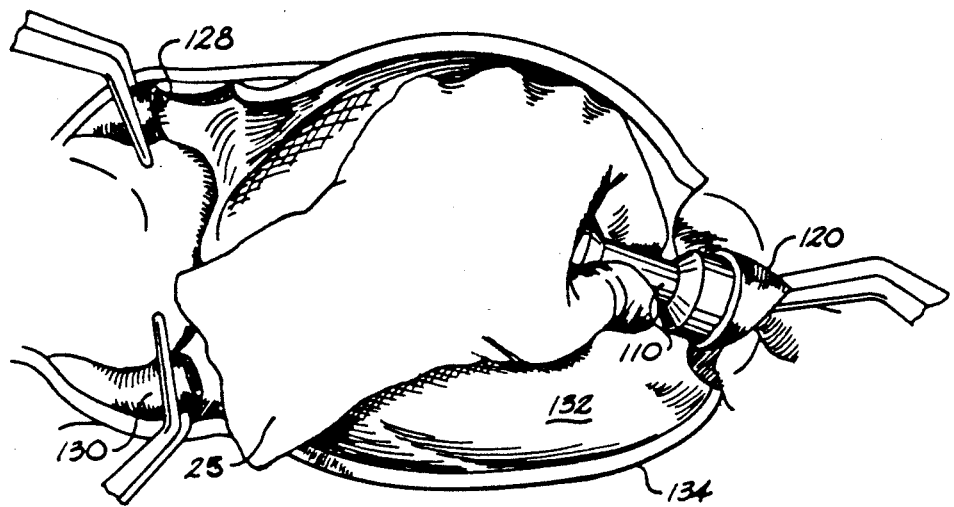
FIG. 1 is plan schematic view of a vessel-sizing gauge being inserted into a resected artery.
Figure 3:
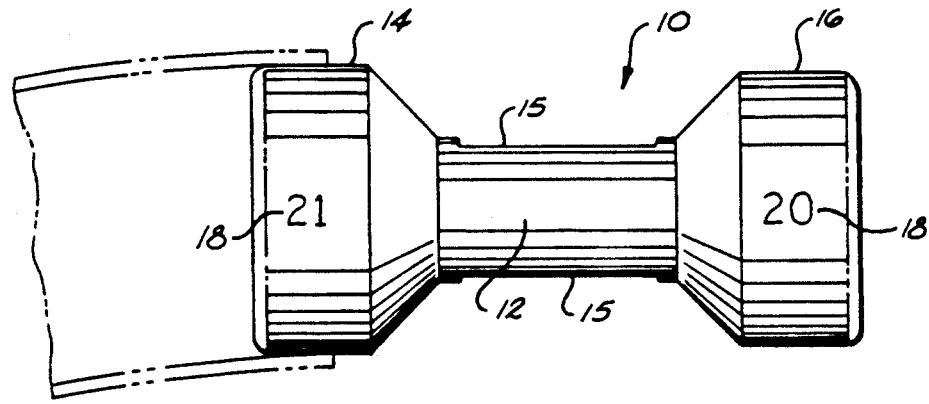
FIG. 3 is a side elevational view of an embodiment of apparatus constructed in accordance with teachings of the present invention for measuring the inside diameter of an exposed vascular vessel end.

Referring now to the figures, the present invention will be described in detail. An intravascular sizing gauge generally 10 is depicted in FIG. 3 having substantially cylindrical elongated handle member 12 on which cylindrical sizing portions or elements 14 and 16 are attached at each end. Scalloped-out flats 15 are preferably provided along opposite sides of elongated handle member 12 to aid in hand manipulation of gauge 10, as illustrated in FIG. 1 during a surgical procedure.

Figure 6:
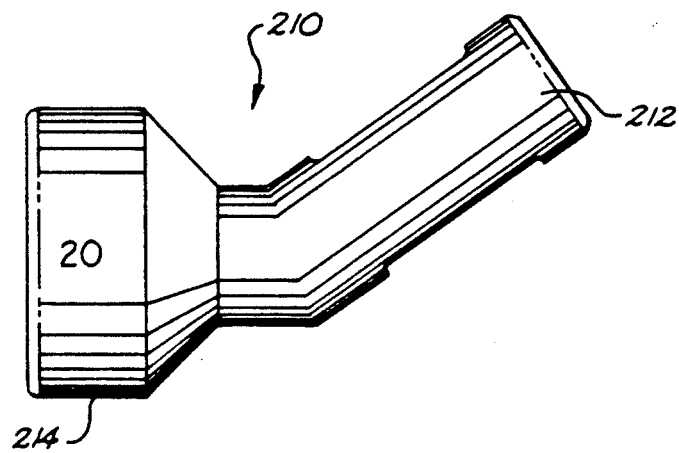
FIG. 6 is a side elevational view of a further embodiment of a sizing apparatus according to the present invention.

Sizing elements 14, 16 are of two different known diameters. Numerical marking indicia 18 is preferably provided on sizing elements 14, 16 corresponding to the diameter of same. Such permits ready visual determination of an appropriate graft size for securement to a measured vessel. Human vascular vessel lumens conventionally range in diameter from about 6 to about 21 centimeters. For full range consideration, it would thus be necessary to provide a set of eight such gauges as illustrated in FIG. 3, most preferably including numerically consecutive diameter portions 14, 16. Likewise, as illustrated in FIG. 6, a gauge 210 may be provided on which only a single cylindrical gauge portion 214 is located at one end of a handle 212. Such embodiment could be employed, for example, with a highly common diameter portion 214 e.g., 20 or 21 centimeters for adults.

Figure 4:
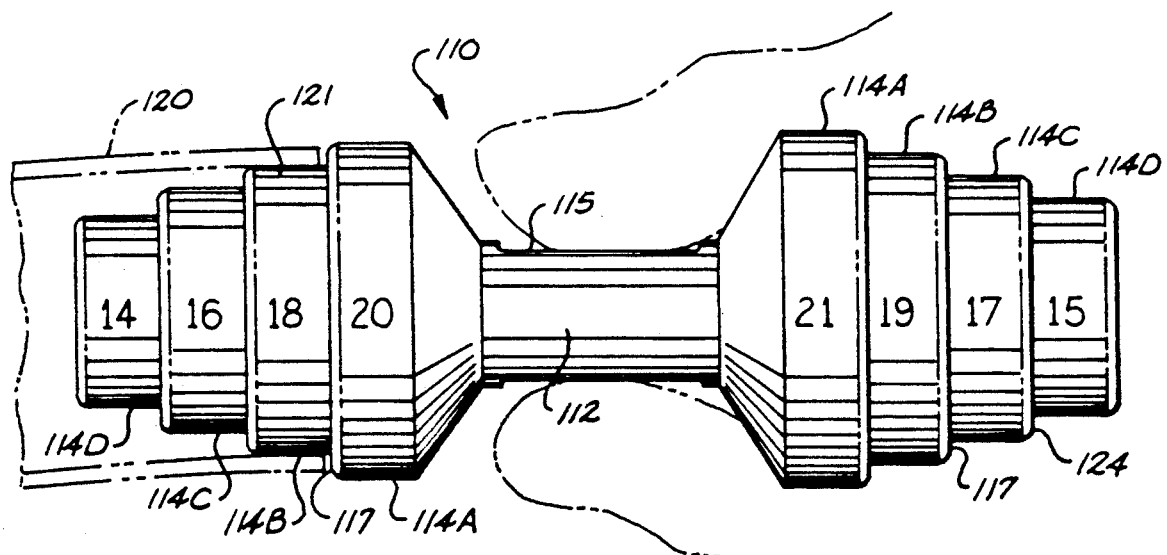
FIGS. 4 and 5 are side elevational views of a preferred embodiment of apparatus constructed in accordance with teachings of the present invention.
Figure 5:
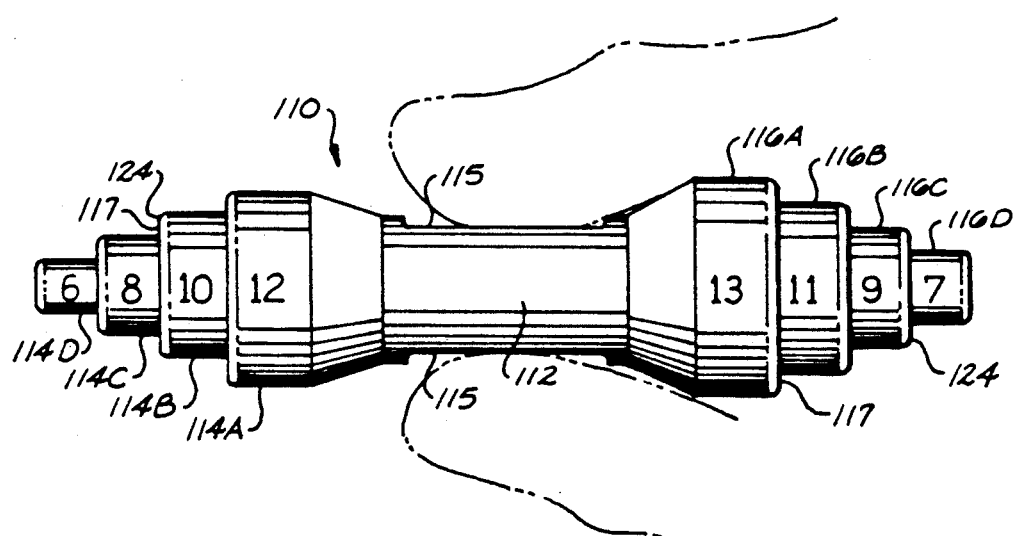

With a preferred gauge structure as illustrated in FIGS. 4 and 5, a lesser total number of gauges is required to form a set adequate to cover the general anatomical range of vessel sizes to be determined. Gauge 110 is provided with a handle portion 112 with opposite gripping means 115 located therealong and with plural sizing portions 114A through 114D and 116A through 116D located at opposite ends of same. Circumferential bevels 124 are also preferably provided at an outer end of each sizing portion 114A-D and 116A-D to assist in insertion of a sizing portion into a vessel 120, with a shoulder 117 located adjacent of each inner bevel 124 against which an exposed end 121 of a vessel 120 may abut (see FIG. 4). Bevels at a forward end of each sizing portion also minimize the possibility of damage to an interior vessel wall. Additionally, since in many surgical procedures, either due to available vessel length or anatomical obstruction, it is necessary that the overall length of sizing portions, 114A-114D and 116A-116D have adequate individual lengths to ensure receipt within the vessel, while at the same time be short enough such that the innermost portions 114D, 116D may be fully receivable within a lumen large enough to receive same. Also as illustrated, each next higher diameter sizing portion is located on an opposite end of gauge 110. Such facilitates general symmetry of gauge 110 and provides a more definite apparent difference in size.

With finger flats, 15, 115, 215, provided on handle members 12, 112, 212, respectively, a surgeon may more easily handle and rotate the sizing apparatus as it is held between the thumb and forefinger. Rotation of the sizing apparatus assists in both insertion and dilation of a vessel.

Individual sizing elements 114A-D and 116A-D are located on handle member 112 in order of decreasing diameters. The two individual sizing portions 114A and 116A having the largest diameters are located immediately adjacent opposite ends of handle member 112. Remaining individual sizing elements are located on opposite ends of sizing gauge 110 so that they extend outwardly from elongated handle member 112 in decreasing order of diameters as noted above. As shown in FIGS. 4 and 5, each of the individual opposite sizing elements 114A-D and 116A-D is one diameter unit separated from its opposite counterpart. The decreasing diameters of the individual sizing elements allow for sizing gauge 110 to be inserted into an existing vessel 120 until one individual element 114A-D or 116A-D snugly fits within the vessel 120. Determination of the diameter of the snug fitting sizing portion allows for a premanufactured artery graft 22, made from Dacron, Gortex, or the like to be readily selected for connection to the artery 120. Such procedure better ensures a successful surgical procedure.

A further embodiment of a sizing apparatus 210 according to the present invention is illustrated in FIG. 6. Sizing apparatus 210 includes a handle means 212 having gripping means, or finger flats 215 located therealong and with a single sizing element 214 located at one end thereof. Further, while all of the other sizing devices described herein have been straight, device 210 is angulated to provide a predetermined angle along a portion of handle means 212. In instances where an effected vessel may be obscured or otherwise difficult to reach with a straight sizing device, a curved device as illustrated in FIG. 6 could be employed.

Figure 2:
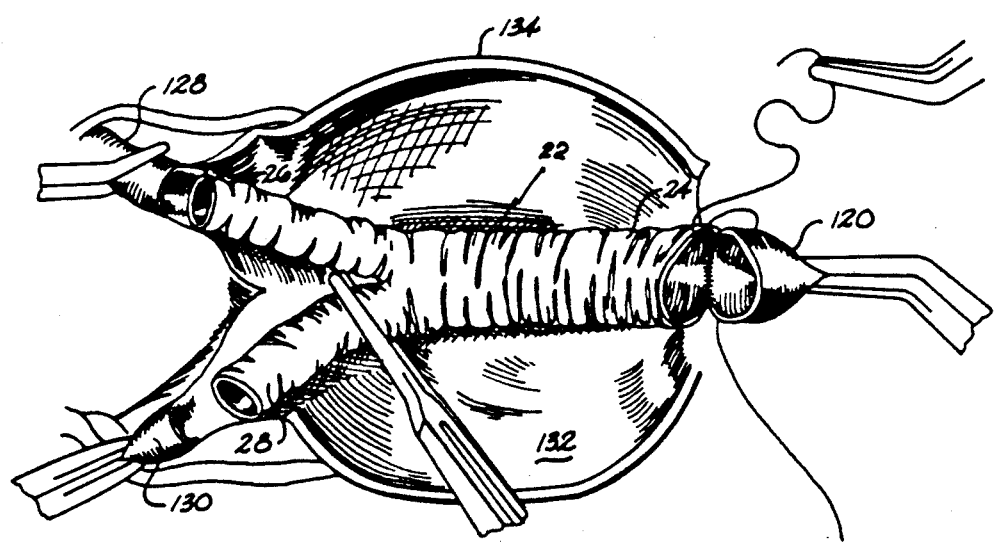
FIG. 2 is a plan schematic illustration of a previously resected artery having one of its openings being secured to a properly sized tubular graft.

The most preferred vessel-sizing gauge 110 is particularly useful in surgery to correct an abdominal aortic aneurysm, as illustrated in FIGS. 1 and 2. Sizing gauge 110 is shown in FIG. 1 being inserted into the lumen of the aorta 120 by a surgeon's hand 25. Arteries 120, 128 and 130 lead into a cavity 132 defined by the wall 134 of an aneurysm, which has been opened and cleaned. Arteries 120, 128 and 130 have been cut and prepared for receiving an artery graft 22. As illustrated, a bifurcated arterial system is effected and a like (bifurcated) graft 22 will be employed. Interior diameters and cross-section of each of arteries 120, 128 and 130 should thus be determined for proper graft sizing. An artery graft 22 is thus obtained having tubes 24, 26 and 28 corresponding in diameter to arteries 120, 128 and 130, respectively. Graft tubes 24, 26 and 28 are then sutured to their respective arteries 120, 128 and 130.

It will be understood, of course, that while the form of the invention herein shown and described constitutes preferred embodiments of the invention, it is not intended to illustrate all possible forms of the invention. Also features of one embodiment may be utilized on other described embodiments. It will also be understood that words used are words of description rather than of limitation, and that various changes may be made without departing from the spirit and scope of the invention herein disclosed.

What is claimed is:

1. An intravascular sizing gauge comprising:
an elongated generally cylindrical handle member, said handle member having flat portions along at least a portion of the length of same for engagement by fingers of a user; and a series of cylindrical sizing portions located at each end of said handle member, said sizing portions being integral with said handle and defining continuous uninterrupted surfaces thereabout, said sizing portions of each series being immediately contiguous and decreasing in diameter towards an outer free end of same, each of said sizing portions having a different known diameter and a beveled edge around an end of same away from said handle member, a forward end of each next adjacent sizing portion defining a shoulder at a rear end of the sizing portion located outwardly with respect to same, said sizing portions being of such length that same are receivable within a vascular lumen for determining diameter and cross-section of the lumen, and said outermost sizing portion on each end defining a generally smooth flat surface across the outer free end of same.

2. A method for sizing an intravascular graft for an effected vessel to which said graft is to be secured comprising the steps of:
(a) preparing the effected vessel for a communicative connection with said graft;

(b) inserting one or more cylindrical sizing portions of known diameter of an intravascular sizing gauge as defined in claim 1 into an open lumen of said vessel until a snug fit is achieved between one said sizing portion and an inside of said vessel;

(c) selecting a graft having openings therein that correspond in size to the size of the lumen as determined by the diameter of the snug fitting sizing portion.

3. An intravascular sizing gauge comprising:

an elongated handle member, and a series of cylindrical sizing portions located at each end of said handle member, said sizing portions being integral with said handle and defining continuous uninterrupted surfaces thereabout, said sizing portions of each series being immediately contiguous and decreasing in diameter towards an outer free end of same, each of said sizing portions having a different known diameter and a beveled edge around an end of same away from said handle member, a forward end of each next adjacent sizing portion defining a shoulder at a rear end of the sizing portion located outwardly with respect to same, said sizing portions being of such length that same are receivable within a vascular lumen for determining diameter and cross-section of the lumen, and said outermost sizing portion on each end defining a generally smooth flat surface across the outer free end of same.

* * * * *